United States Patent [19]

St. Clair et al.

[11] 3,962,440

[45] June 8, 1976

[54] QUINOXALINE COMPOUNDS AS HYPNOTIC AGENTS

[75] Inventors: Roger L. St. Clair, New Palestine; Thomas D. Thibault, Indianapolis, both of Ind.

[73] Assignee: Eli Lilly and Company, Indianapolis, Ind.

[22] Filed: Dec. 26, 1973

[21] Appl. No.: 427,948

[52] U.S. Cl. .................................................. 424/250
[51] Int. Cl.$^2$ ....................................... A61K 31/495
[58] Field of Search ..................... 424/250; 260/250

[56] References Cited
UNITED STATES PATENTS

| | | | |
|---|---|---|---|
| 3,133,056 | 5/1964 | Ash et al. | 260/239.3 |
| 3,594,418 | 7/1971 | Gilbert | 260/575 |

OTHER PUBLICATIONS

Beilstein 24 p. 380-381
Chem. Abst. 44 – 3501 (1950); Chem. Abst. 74 – 77071j (1971); Chem. Abst. 48 – 11427g–11428 (1954).
Chem. Abst. 55 – 18741h (1961).
Chem. Abst. 52 – 18428i (1958).
Chem. Abst. 52 18721h (1958).
Chem. Abst. 59 – 1268d (1965).
Chem. Abst. 71 – 91366d (1969).
Chem. Abst. 73 – 66614s (1970).
Chem. Abst. 73 – 66618w (1970).
Chem. Abst. 74 – 10010e (1971).
Chem. Abst. – 57 – 1073h (1962).
Chem. Abst., 53 – 13160g (1959).

*Primary Examiner*—Stanley J. Friedman
*Attorney, Agent, or Firm*—Kathleen R. S. Page; Everet F. Smith

[57] ABSTRACT

The present invention is concerned with the use of certain quinoxaline compounds as hypnotic agents.

22 Claims, No Drawings

QUINOXALINE COMPOUNDS AS HYPNOTIC AGENTS

SUMMARY OF THE INVENTION

The quinoxaline compounds serving as hypnotic agents in the present invention are 2(1H), 3(4H)-quinoxalinedione compounds of the formula:

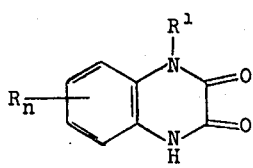

wherein n represents 0, 1, or 2; each R independently represents
1. loweralkyl of $C_1$–$C_4$,
2. loweralkoxy of $C_1$–$C_4$,
3. loweralkylthio of $C_1$–$C_4$,
4. cyclopropyl,
5. bromo,
6. chloro,
7. fluoro,
8. nitro,
9. cyano,
10. fluoroalkyl of $C_1$–$C_2$,
11. amino, or
12. amino mono or disubstituted with loweralkyl of $C_1$–$C_4$, each independently selected; subject to the limitation that R can represent bromo or chloro only when n represents 2 and one R represents a moiety other than bromo or chloro; and $R^1$ represents
1. H or
2. methyl;
and the pharmaceutically acceptable alkali metal and alkaline earth metal salts.

The present invention is directed to methods employing and compositions comprising these compounds. Certain of the compounds are also claimed as novel compounds.

DETAILED DESCRIPTION OF THE INVENTION

The compounds to be employed in accordance with the present invention are prepared in accordance with conventional procedures. Those of the compounds wherein $R^1$ represents H are prepared by condensing an appropriately-substituted o-phenylenediamine with an oxalate, preferably diethyl oxalate:

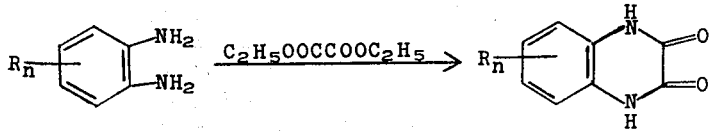

The reaction goes forward at temperatures of 50°–100°C., but is more advantageously conducted at reflux temperatures. An inert liquid can be employed as reaction medium, but inasmuch as diethyl oxalate is a liquid, it is preferred to employ the same in excess, to serve as reaction medium. Typically the product precipitates in the reaction mixture. Separation and, if desired, purification, are carried out in conventional procedures.

The foregoing method is generally available regardless of the indentity of R. However, where R represents cyclopropyl, cyano, or difluoroalkyl, the compounds of the present invention are often preferably prepared by an alternate reaction:

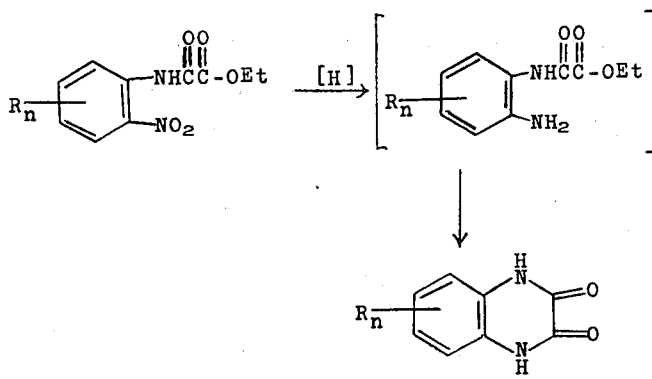

in which the nitro group is initially reduced and the resulting compound cyclizes to the desired quinoxalinedione compound. The reaction is conducted in conventional procedures.

Those of the compounds wherein $R^1$ = methyl are prepared in yet another procedure. In this procedure, an appropriately-substituted 1-methyl-2-quinoxalinone is further oxidized to the dione:

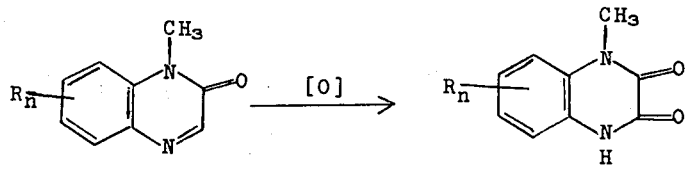

The identity of oxidizing agent is not critical, but hydrogen peroxide in acetic acid has been found to give good results. The reaction goes forward at temperatures of 0°–50°C., but is most conveniently conducted at room temperatures.

In the foregoing reaction routes, the identity of R remains constant throughout the synthesis. As will be evident to those skilled in the art, various reactions are available by which one R group can be converted to another R group. Such conversion can be made with the quinoxalinediones or with precursors in the synthetic routes described hereinbelow.

Salts are also prepared in conventional procedures, typically by the reaction of stoichiometric amounts of compound and a suitable base in a liquid reaction medium. Analyses of salts indicate that a compound of the present invention acts as only a monoprotic acid. For example, a salt prepared with excess potassium hydroxide exists as only the monopotassium salt; and the stoichiometry with this and other alkali metals is 1:1. Likewise, two equivalents of a compound of the present invention react with one equivalent of calcium hydroxide to yield a representative alkaline earth metal salt in which the stoichiometry is 2:1 (compound:base).

The compounds to be employed in accordance with the present invention readily form solvates with water or solvents such as formamide, N-methylformamide, N,N-dimethylformamide, N,N-dimethylacetamide, and N-methylpyrrolidine. Therefore, the compounds can be employed in the practices of the present invention in such solvate form.

Preferred compounds to be employed in accordance with the present invention are those of the formula

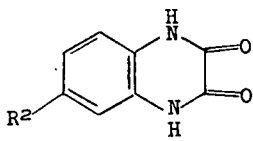

wherein $R^2$ represents methyl, ethyl, or fluoroalkyl of $C_1-C_2$, and the pharmaceutically acceptable alkali metal and alkaline earth metal salts. Even more preferred are those compounds of the formula

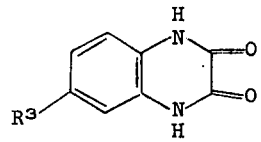

wherein $R^3$ represents fluoroalkyl of $C_1-C_2$, and the pharmaceutically acceptable alkali metal and alkaline earth metal salts. A particularly preferred compound is 6-trifluoromethyl-2(1H), 3(4H)-quinoxalinedione and its pharmaceutically acceptable alkali metal and alkaline earth metal salts.

The compounds to be employed in accordance with the present invention have been named as 2(1H), 3(4H)-quinoxalinediones. However, as will be understood by those skilled in the art, these compounds may tautomerize:

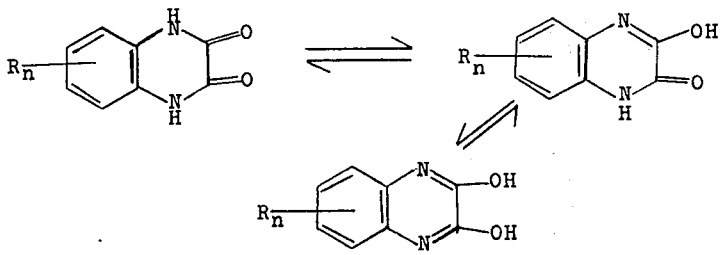

While the dione structure is uniformly assumed for purposes of nomenclature, the conversion to either or both of the alternate forms will not alter the efficacy of the compounds in accordance with the present invention.

The following examples describe the preparation of the compounds to be employed in accordance with the present invention.

EXAMPLE 1

2(1H), 3(4H)-QUINOXALINEDIONE o-Phenylenediamine (10 grams) and ethyl oxalate (100 ml.) were mixed and the mixture was heated, with stirring, to reflux and refluxed for 30 minutes. The reaction mixture was then cooled and the resulting precipitate, the desired 2(1H), 3(4H)-quinoxalinedione, was separated by filtration. The product did not melt below 400°C. It was recrystallized from a mixture of dimethylformamide and water, yielding a purified product which did not melt below 405°C. The identity of the product was confirmed by NMR and IR. Elemental analysis showed Analysis, Calc. for $C_8H_6N_2O_2$: C, 58.9; H, 3.7; N, 17.51. Found: C, 58.66; H, 3.81; N, 17.38.

EXAMPLE 2

6-TRIFLUOROMETHYL-2(1H), 3(4H)-QUINOXALINEDIONE

4-Trifluoromethyl-o-phenylenediamine (8.0 grams) was added to 80 ml. of ethyl oxalate and the resulting mixture was heated to reflux and refluxed for two hours. A precipitate formed during this period. The reaction mixture was then cooled to room temperature and filtered to separate the precipitate, m.p. 344°–346°C. (dec.) The product was identified as the expected 6-trifluoromethyl- 2(1H), 3(4H)-quinoxalinedione, by IR, TLC, NMR, and microanalysis.

Analysis, Calc for $C_9H_5N_2O_2F_3$: C, 46.97; H, 2.19; N, 12.17; F, 24.76. Found: C, 47.18; H, 2.36; N, 12,09; F, 25.06.

EXAMPLE 3

6-DIFLUOROMETHYL-2(1H), 3(4H)-QUINOXALINEDIONE

Ethyl N-(4-difluoromethyl-2-nitrophenyl)oxamide (1.0 gram) was hydrogenated in 200 ml. of ethanol over 150 mg. of platinum oxide. The reaction mixture was then evaporated to dryness and the residue heated with ethanol, producing a solid. It was collected and recrystallized from ethanol. Two crops of the desired 6-trifluoromethyl-2(1H), 3(4H)-quinoxalinedione product were obtained: m.p. about 330°C. (darkening, 290°C.) and m.p. about 330 (darkening, 280°C.). The crops were combined for microanalysis.

Analysis, Calc. for $C_9H_6F_2N_2O_2$: C, 50.95; H, 2.85; N, 13.20; F, 17.91. Found: C, 50.86; H, 3.11; N, 13.00; F, 18.14.

EXAMPLE 4

1-METHYL-2(1H), 3(4H)-QUINOXALINEDIONE

1-Methyl-2(1H)-quinoxalinone (5.3 grams) was allowed to stand at room temperature for 72 hours in a mixture of 60 ml. of acetic acid and 35 ml. of 30 percent hydrogen peroxide. The product separated out as needles after 48 hours. After 72 hours, no starting material was detectable in the supernatant liquid by TLC (ethyl acetate). The product was separated and washed sequentially with water and with ethanol, m.p. 287°–289°C. It was then recrystallized from water, 287°–290°C. (literature: 286°–287°C, G. W. H. Cheeseman, *J. Chem. Soc.* 1804 (1955); 285°–286°C., G. W. H. Cheeseman, *J. Chem. Soc.* 1246 (1961)). NMR also confirmed the identity of the product.

EXAMPLE 5

1-METHYL-7-TRIFLUOROMETHYL-2(1H), 3(4H)-QUINOXALINEDIONE

1-Methyl-7-trifluoromethyl-2(1H)-quinoxalinone (2.68 grams) was dissolved in 20 ml. of acetic acid and 20 ml. of 30 percent hydrogen peroxide were added. The reaction mixture was held at room temperature for 24 hours, by which time a solid had separated out. It was collected by filtration. NMR and microanalysis confirmed that the product was 1-methyl-7-trifluoromethyl-2(1H), 3(4H)-quinoxalinedione. The product melted at 283°–287°C.

Analysis, Calc. for $C_{10}H_7F_3N_2O_2$: C, 49.19; H, 2.89; N, 11.47; F, 23.34. Found: C, 48.92; H, 3.07; N, 11.72; F, 23.04.

EXAMPLE 6

6-TRIFLUOROMETHYL-2(1H), 3(4H)-QUINOXALINEDIONE, MONOPOTASSIUM SALT, MONOHYDRATE

6-Trifluoromethyl-2(1H), 3(4H)-quinoxalinedione (2.3 grams) was slurried in 25 ml. of methanol and 5 ml. of water and treated with 20 ml. of 1N potassium hydroxide in methanol. Precipitation began even before the solution was complete. The mixture was warmed on a steam bath to complete the solution, then filtered and refrigerated. A colorless solid precipitated and was collected and dried, m.p. >300°. The product was analyzed and its identity confirmed as 6-trifluoromethyl-2(1H), 3(4H)-quinoxalinedione, monopotassium salt, monohydrate. Analysis for water showed 6.6 percent (theoretical, 6.3 percent); TLC showed only one spot; analysis for potassium (by atomic absorption) showed 100 percent; and the molecular weight (by non-aqueous titration) was 100.8 percent of the theoretical.

EXAMPLE 7

6-TRIFLUOROMETHYL-2(1H), 3(4H)-QUINOXALINEDIONE 1:1 SOLVATE WITH DIMETHYLACETAMIDE

6-Trifluoromethyl-2(1H, 3(4H)-quinoxalinedione (1100 grams) was dissolved in 8 liters of dimethylacetamide and 3.5 liters of water were added. The reaction mixture was stirred and cooled to room temperature. A solid precipitated and was separated by filtration and washed with 2 liters of 70 percent dimethylacetamide. The product was identified as a 1:1 solvate of 6-trifluoromethyl- 2(1H), 3(4H)-quinoxalinedione with dimethylacetamide.

EXAMPLES 8–32

Other representative compounds to be employed in accordance with the present invention were prepared by analogous procedures. These compounds were as follows:

6-methyl-2(1H), 3(4H)-quinoxalinedione, m.p. 342°–345°C. Analysis, Calc. for $C_9H_8N_2O_2$: C, 61.36; H, 4.58; N, 15.90. Found: C, 61.12; H, 4.87; N, 15.66.

6,7-dimethyl-2(1H), 3(4H)-quinoxalinedione, m.p., >400°C. Analysis, Calc. for $C_{10}H_{10}N_2O_2$: C, 63.15; H, 5.30; N, 14.73. Found: C, 63.30; H, 5.44; N, 14.63.

5-fluoro-2(1H), 3(4H)-quinoxalinedione, m.p., 367°C. (dec). Analysis, Calc. for $C_8H_5N_2O_2F$: C, 53.34; H, 2.80; N, 15.55; F, 10.55. Found: C, 53.05; H, 2.81; N, 15.33; F, 10.60.

6-ethyl-2(1H), 3(4H)-quinoxalinedione, m.p., 344°C. (dec). Analysis, Calc. for $C_{10}H_{10}N_2O_2$: C, 63.15; H, 5.30; N, 14.73. Found: C, 62.90; H, 5.47; N, 14.94.

5-methyl-2(1H), 3(4H)-quinoxalinedione, m.p., 352°C. (dec). Identity was confirmed by mass spectroscopy, whicn showed a molecular ion of 176, identical with the theoretical molecular weight of the compound, 176.

6-fluoro- 2(1H), 3(4H)-quinoxalinedione, m.p., 387°–390°C. (dec). Analysis, Calc. for $C_8H_5N_2O_2F$: C, 53.34; H, 2.80; N, 15.55; F, 10.55. Found: C, 53.58; H, 2.86; N, 15.30; F, 10.74.

5-trifluoromethyl-2(1H), 3(4H)-quinoxalinedione, m.p., 277°–280°C. (dec). Analysis, Calc. for $C_9H_5F_3N_2O_2$: C, 46.97; H, 2.19; N, 12.17; F, 24.76. Found: C, 47.15; H, 2.26; N, 12.28; F, 24.74.

6-methylthio-2(1H), 3(4H)-quinoxalinedione, m.p., 330°–333°C. Analysis, Calc. for $C_9H_8N_2O_2S$: C, 51.91; H, 3.87; N, 13.45; S, 15.40. Found: C, 51.66; H, 3,82; N, 13.62; S, 15.17.

6-pentafluoroethyl-2(1H), 3(4H)-quinoxalinedione, m.p., 339°–341°C. Analysis, Calc. for $C_{10}H_5F_5N_2O_2$: C, 42.87; H, 1.80; F, 33.91; N, 10.00. Found: C, 43.15; H, 1.81; F, 33.90; N, 10.01.

6-diethylamino-2(1H), 3(4H)-quinoxalinedione, m.p., 325°–327°C. Analysis, Calc. for $C_{12}H_{15}N_3O_2$: C, 61.80; H, 6.43; N, 18.02. Found: C, 62.00; H, 6.33; N, 18.06.

6-n-propyl-2(1H), 3(4H)-quinoxalinedione, m.p. 348°–350°C. Analysis, Calc. for $C_{11}H_{12}N_2O_2$: C, 64.69; H, 5.92; N, 13.72. Found: C, 64.67; H, 5.72; N, 13.52.

6-isopropyl-2(1H), 3(4H)-quinoxalinedione, m.p., 344°–345°C. Analysis, Calc. for $C_{11}H_{12}N_2O_2$: C, 64.69; H, 5.92; N, 13.72. Found: C, 64.81; H, 5.86; N, 13.70.

6-cyano-2(1H), 3(4H)-quinoxalinedione, m.p., >360°C. Analysis, Calc. for $C_9H_5N_3O_2$: C, 57.76; H, 2.69; N, 22.45. Found: C, 57.52; H, 2.95; N, 22.22.

6-fluoromethyl-2(1H), 3(4H)-quinoxalinedione, m.p., 270°C. (dec). Analysis, Calc. for $C_9H_7FN_2O_2$: C, 55.67; H, 3.63; N, 14.43; F, 9.78. Found: C, 55.78; H, 3.85; N, 14.25; F, 9.75.

6-tert-butyl-2(1H), 3(4H)-quinoxalinedione, m.p., 375°–378°C. Analysis, Calc. for $C_{12}H_{14}N_2O_2$: C, 66.04; H, 6.47; N, 12.84. Found: C, 65.86; H, 6.21; N, 12.73.

6-methoxy-2(1H), 3(4H)-quinoxalinedione, m.p., 354°–356°C. Analysis, Calc. for $C_9H_8N_2O_3$: C, 56.25; H, 4.20; N, 14.58. Found: C, 56.50; H, 4.44; N, 14.48.

5-nitro-2(1H), 3(4H)-quinoxalinedione, m.p., 284°–285°C. (dec). Analysis, Calc. for $C_8H_5N_3O_4$: C, 46.39; H, 2.43; N, 20.29. Found: C, 46.40; H, 2.62; N, 20.04.

7-chloro-5-nitro-2(1H), 3(4H)-quinoxalinedione, M.P., 320°–323°C. Analysis, Calc. for C₈H₄ClN₃O₄: C, 39.77; H, 1.67; N, 17.39; Cl, 14.67. Found: C, 39.60; H, 1.82; N, 17.52; Cl, 14.76.

5,7-dimethyl-2(1H), 3(4H)-quinoxalinedione, m.p., 330°–332°C. Analysis, Calc. for C₁₀H₁₀N₂O₂: C, 63.15; H, 5.30; N, 14.73. Found: C, 62.92; H, 5.56; N, 14.55.

5-nitro-7-trifluoromethyl-2(1H), 3(4H)-quinoxalinedione, m.p., 342°–344°C. Analysis, Calc. for C₉H₄F₃N₃O₄: C, 39.29; H, 1.47; N, 15.27; F, 20.71. Found: C, 39.41; H, 1.66; N, 15.23; F, 20.96.

5-amino-7-trifluoromethyl-2(1H), 3(4H)-quinoxalinedione, m.p. 337°–339°C. Analysis, Calc. for C₉H₆F₃N₃O₂: C, 44.09; H, 2.47; N, 17.14; F, 23.25. Found: C, 44.37; H, 2.80; N, 17.20; F, 23.15.

6-cyclopropyl-2(1H), 3(4H)-quinoxalinedione, m.p., >360°C. Analysis, Calc. for C₁₁H₁₀N₂O₂: C, 65.34; H, 4.98; N, 13.85. Found: C, 65.14; H, 4.75; N, 13.93.

6-n-butyl-2(1H), 3(4H)-quinoxalinedione, m.p., 326°–327°C. Analysis, Calc. for C₁₂H₁₄N₂O₂: C, 66.04; H, 6.47; N, 12.82. Found: C, 66.30; H, 6.20; N, 13.12.

5,7-bis(trifluoromethyl)-2(1H), 3(4H)-quinoxalinedione, m.p., 333°C. Analysis, Calc. for C₁₀H₄F₆N₂O₂: C, 40.29; H, 1.35; N, 9.40; F, 38.23. Found: C, 40.32; H, 1.40; N, 9.65; F, 38.48.

6-(1,1-difluoroethyl)-2(1H), 3(4H)-quinoxalinedione, m.p., >300°C. (dec). Analysis, Calc. for C₁₀H₈F₂N₂O₂: C, 53.10; H, 3.57; N, 12.39; F, 16.80. Found: C, 52.88; H, 3.51; N, 12.16; F, 16.70.

As set forth above, the compounds which serve as the active agent in accordance with the present invention exhibit hypnotic activity in warm-blooded animals. The compounds can be utilized in any of the many therapeutic situations calling for a hypnotic. They can be administered to animals, particularly human beings, in which it is desired to induce sleep. They can also be used to induce sleep in animals who, because of emotional or physiological disorders, suffer from insomnia. Accordingly, the present invention is directed to a method for causing a hypnotic effect in a warm-blooded animal, which method comprises administering to a warm-blooded animal an effective amount of the present active agent.

The exact amount of the present active agent which is employed is not critical and will vary with such factors as the particular compound employed and whether it is supplied as a salt or solvate; the particular species of animal; and the nature of the particular therapeutic situation. In general, doses of 0.1 to 250 mg./kg. give good results; with many compounds, doses of from 1 to 100 mg./kg. give good results. These doses are based on the compounds per se; if the compounds are employed as salts; solvates, or both, correspondingly higher amounts will be needed to supply the same dose of active moiety.

The compounds can be employed as such, but are preferably formulated in conventional pharmaceutical procedures. In general, oral administration is preferred. Suitable formulations include powders, elixirs, syrups, drops, capsules, tablets, or coated tablets which provide sustained or delayed release. A preferred formulation is a pharmaceutical formulation in dosage unit form adapted for administration to obtain a hypnotic effect, comprising, per dosage unit, a hypnotically-effective non-toxic amount within the range from about 10 to about 1000 milligrams of at least one of the present active agents. An even more preferred formulation is that wherein the active agent is a compound of the formula

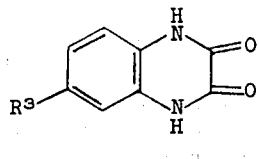

wherein R³, as above, is fluoroalkyl of C₁–C₂, or a pharmaceutically acceptable alkali metal or alkaline earth metal salt.

In addition, the compounds can be formulated in polyethylene glycol or polyvinylpyrrolidone. In a representative procedure, 6-trifluoromethyl-2(1H), 3(4H)-quinoxalinedione was dissolved in methanol and polyvinylpyrrolidone added. The methanol was then evaporated, yielding a solid solution of 6-trifluoromethyl-2(1H), 3(44H)quinoxalinedione and polyvinylpyrrolidone. Such solutions were made with proportions ranging from 6:1 to 2:1 (PVP:6-trifluoromethyl-2(1H), 3(4H)-quinoxalinedione).

EXAMPLES 33–62

Representative compounds to be employed in accordance with the present invention were evaluated as hypnotics in a test procedure employing canaries. In this procedure, canaries weighing from about 15 to about 23 grams, of mixed sexes but principally female, were used. Three canaries were employed for each compound, except for several tests (marked below) employing six canaries. Each compound was formulated in water with a small amount of acacia as suspending agent. Administration of the resulting suspension was by the oral route.

Each group of canaries was observed every five minutes during the hour compound administration. Results were recorded as the number of canaries which slept, and the average time slept per group of canaries. Results were as reported in the following table.

TABLE I

| Compound | Dose in mg./kg. | | | | | | | | | | | |
|---|---|---|---|---|---|---|---|---|---|---|---|---|
| | 160 | | 80 | | 40 | | 20 | | 10 | | 5 | |
| | No. | Min. | No. | Min. | No. | Min. | No. | Min. | No. | Min. | No. | Min. |
| 2(1H), 3(4H)-quinoxalinedione | — | — | 3 | 38 | 2 | 18 | 0 | — | — | — | — | — |
| 6-methyl-2(1H), 3(4H)-quinoxalinedione | — | — | 3 | 52 | 3 | 32 | 2 | 10 | 0 | — | 0 | — |
| 6,7-dimethyl-2(1H), 3(4H)-quinoxalinedione | — | — | 3 | 48 | 3 | 30 | 0 | — | — | — | — | — |
| 5-fluoro-2(1H), 3(4H)-quinoxalinedione | — | — | 1 | 5 | 3 | 10 | 0 | — | — | — | — | — |

TABLE I – Continued

| Compound | Dose in mg./kg. | | | | | | | | | | | |
|---|---|---|---|---|---|---|---|---|---|---|---|---|
| | 160 | | 80 | | 40 | | 20 | | 10 | | 5 | |
| | No. | Min. | No. | Min. | No. | Min. | No. | Min. | No. | Min. | No. | Min. |
| 6-ethyl-2(1H), 3(4H)-quinoxalinedione | — | — | 3 | 47 | 3 | 43 | 2 | 13 | 0 | — | — | — |
| 6-trifluoromethyl-2(1H), 3(4H)-quinoxalinedione | — | — | 3 | 50 | 3 | 47 | 2 | 7 | 1 | 2 | 0 | — |
| 5-methyl-2(1H), 3(4H)-quinoxalinedione | — | — | 3 | 33 | 2 | 10 | 0 | — | — | — | — | — |
| 6-fluoro-2(1H), 3(4H)-quinoxalinedione | — | — | 3 | 18 | 2 | 10 | 1 | 3 | 0 | — | — | — |
| 5-trifluoromethyl-2(1H), 3(4H)-quinoxalinedione | — | — | 1 | $2^d$ | — | — | — | — | — | — | — | — |
| 6-difluoromethyl-2(1H), 3(4H)-quinoxalinedione | — | — | 3 | $30^d$ | 3 | $20^d$ | $2^e$ | $1^d$ | — | — | — | — |
| 6-methylthio-2(1H), 3(4H)-quinoxalinedione | — | — | 1 | $2^d$ | 0 | $—^d$ | — | — | — | — | — | — |
| 6-pentafluoroethyl-2(1H), 3(4H)-quinoxalinedione | — | — | 3 | 45 | $1^e$ | $1^d$ | 0 | — | — | — | — | — |
| 6-diethylamino-2(1H), 3(4H)-quinoxalinedione | 2 | $8^d$ | 1 | $3^d$ | — | — | — | — | — | — | — | — |
| 6-n-propyl-2(1H), 3(4H)-quinoxalinedione | 2 | $15^d$ | 2 | $13^d$ | 1 | 5 | 1 | 2 | 0 | — | — | — |
| 6-isopropyl-2(1H), 3(4H)-quinoxalinedione | — | — | 2 | $27^d$ | 3 | $38^d$ | 0 | $—^d$ | — | — | — | — |
| 6-cyano-2(1H), 3(4H)-quinoxalinedione | — | — | 1 | $5^d$ | 2 | $8^d$ | $1^e$ | $4^d$ | 0 | — | 0 | — |
| 6-fluoromethyl-2(1H), 3(4H)-quinoxalinedione | — | — | 1 | $12^d$ | — | — | 3 | $49^d$ | 3 | $30^d$ | 2 | $10^d$ |
| 6-tert-butyl-2(1H), 3(4H)-quinoxalinedione | — | — | 3 | $10^d$ | 0 | — | — | — | — | — | — | — |
| 7-trifluoromethyl-1-methyl-2(1H), 3(4H)-quinoxalinedione | — | — | 3 | $15^d$ | 2 | $20^d$ | 0 | — | — | — | — | — |
| 6-methoxy-2(1H), 3(4H)-quinoxalinedione | — | — | 3 | 35 | 2 | 23 | 0 | — | — | — | — | — |
| 5-nitro-2(1H), 3(4H)-quinoxalinedione | — | — | 3 | 35 | 3 | 32 | 0 | — | — | — | — | — |
| 7-chloro-5-nitro-2(1H), 3(4H)-quinoxalinedione | — | — | — | — | 3 | 38 | 3 | 18 | 0 | — | — | — |
| 5,7-dimethyl-2(1H), 3(4H)-quinoxalinedione | — | — | 3 | 15 | 0 | — | — | — | — | — | — | — |
| 5-nitro-7-trifluoromethyl-2(1H), 3(4H)-quinoxalinedione | — | — | 3 | 48 | 3 | 55 | 3 | 32 | 0 | — | — | — |
| 5-amino-7-trifluoromethyl-2(1H), 3(4H)-quinoxalinedione | — | — | 3 | 35 | 3 | 13 | 0 | — | — | — | — | — |
| 1-methyl-2(1H), 3(4H)-quinoxalinedione | — | — | 2 | 22 | 0 | — | — | — | — | — | — | — |
| 6-cyclopropyl-2(1H), 3(4H)-quinoxalinedione | — | — | 3 | $40^d$ | 3 | $25^d$ | 1 | $13^d$ | 0 | $—^d$ | — | — |
| 6-n-butyl-2(1H), 3(4H)-quinoxalinedione | — | — | 3 | $18^d$ | 3 | $5^d$ | 0 | $—^d$ | — | — | — | — |
| 5,7-bis(trifluoromethyl)-5,7-bis)trifluoromethyl)-2(1H), 3(4H)-quinoxalinedione | — | — | 3 | $30^d$ | 3 | $23^d$ | 3 | $7^d$ | 0 | — | — | — |
| 6-(1,1-difluoroethyl)-2(1H), 3(4H)-quinoxalinedione | — | — | 3 | $32^d$ | 3 | $15^d$ | 0 | $—^d$ | — | — | — | — |

$^d$ = one or more animals drowsy
$^e$(as superscript) = group of 6 canaries

EXAMPLES 63–67

Representative compounds to be employed in accordance with the present invention were evaluated in cats.

Adult cats were employed, each serving as its own "control." To determine control values, an electroencephalogram was made on each cat for a period of 2 hours and 10 minutes of sleep. This procedure was carried out a total of three times for each animal. The resulting electroencephalograms were analyzed to determine the number of minutes for each type of sleep:

1. awake
2. drowsy
3. light sleep
4. light to deep sleep ⎫
5. deep sleep           ⎬ (grouped together as slow wave sleep ("SWS")) sleep
6. REM (rapid eye movement)

The three times for each kind of sleep were averaged, yielding for each cat average (control) times for each type of sleep. At regular intervals between treatment, a single additional control was run, as described above. Control values were then updated, always averaging the three latest sets of control data.

Each of the respective compounds was administered orally by stomach tube: the compound was formulated in an aqueous solution with acacia as suspending agent. Beginning 10 minutes after compound administration and continuing for 2 hours and 10 minutes, electroencephalograms were conducted as in the controls, and the data were similarly processed.

The percent change between treatment and control values was calculated for each of three periods: awake, SWS, and REM. "Sleep latency," the time (in minutes) between compound administration and onset of sleep, was also recorded for many of the compounds. The results were as reported below in Table II.

TABLE II

| Compound | Sleep latency in min. | Dose in mg./kg. | Percent Change Awake | SWS | REM |
|---|---|---|---|---|---|
| 5-methyl-2(1H), 3(4H)-quinoxalinedione: Cat No. 1 | 55 | 2 | +39 | −28.6 | −62.6 |
| " | 32 | 0.5 | +11 | −41 | −34 |
| " | 38 | 1.0 | +80 | +26 | −27 |
| " | 23 | 4.0 | +123 | −24 | −61 |
| " | 19 | 8.0 | +25 | −32 | −12.6 |
| Cat. No. 2 | not recorded | 2 | +195 | −76 | −86 |
| " | <10 | 1 | −52 | +21 | no change |
| " | 25 | 4 | +92 | −38 | −61 |
| " | 20 | 8 | −44 | −11 | +82 |
| 6-ethyl-2(1H), 3(4H)-quinoxalinedione: Cat No. 1 | not recorded | 2 | −40 | +15 | no change |
| " | " | 4 | − 5 | −25 | no change |
| " | <10 | 1 | −19 | +15 | no change |
| " | 13 | 8 | +32 | +7 | no change |
| " | 11 | 16 | −49 | +71 | no change |
| Cat No. 2 | 22 | 1 | −13 | +35 | − 8 |
| " | <10 | 4 | −18 | +22 | −17 |
| " | 14 | 2 | no change | +26 | +34 |
| " | 15 | 8 | no change | +12 | −20 |
| 6-methyl-2(1H), 3(4H)-quinoxalinedione: Cat No. 1 | 20 | 4 | +28 | − 4 | − 6 |
| " | 21 | 2 | +61 | − 6 | −51 |
| " | 19 | 8 | no change | +46 | −27 |
| " | 22 | 1 | −53 | +41 | − 8 |
| " | 24 | 16 | −33 | +64 | −43 |
| Cat No. 2 | 17 | 1 | −28 | +24 | no change |
| " | 14 | 4 | −20 | +26 | −58 |
| " | 10 | 2 | −63 | +63 | −16 |
| " | 19 | 8 | +148 | −51 | −100 |
| " | not recorded | 16 | +195 | −84 | −100 |
| Cat No. 3 (compound formulated in polyethylene glycol 200 instead of usual procedure) | 39 | 1 | − 9 | +110 | +130 |
| Cat No. 4 | 10 | 1 | −16 | + 7.6 | +81 |
| " | <10 | 4 | −11 | +13 | +16 |
| " | 14 | 8 | −45 | +43 | +64 |
| " | 31 | 16 | no change | + 7.7 | +28 |
| " | 13 | 2 | −11 | +12 | +64 |
| Cat No. 5 | 12 | 2 | +24 | +40 | −47 |
| " | 25 | 0.5 | +67 | −40 | −18 |
| " | <10 | 4 | −33 | +29 | no change |
| " | 41 | 1 | +74 | −22 | +46 |
| " | 24 | 8 | −36 | +59 | +39 |
| " | 35 | 16 | −28 | +41 | +39 |
| Cat No. 6 | 22 | 2 | +35 | +6.2 | −55 |
| " | 18 | 1 | +26 | −42 | −17 |
| " | 33 | 4 | +82 | −30 | −39 |
| " | not recorded | 8 | +78 | −21 | −48 |
| " | 32 | 16 | +16 | −14 | −24 |
| Cat No. 7 | 41 | 2 | +10 | −75 | −100 |
| " | not recorded | 4 | +4 | −100 | −100 |
| " | " | 16 | −15 | −90 | −100 |
| " | " | 8 | −38 | −28 | −100 |
| 2(1H), 3(4H)-quinoxalinedione: Cat No. 1 | not recorded | 2 | +17 | +13.5 | −24.9 |
| " | 33 | 1 | +78 | −24 | no change |
| " | 23 | 0.5 | +65 | −36 | +13 |
| " | 29 | 4 | +45 | −12.3 | −14 |
| " | 49 | 8 | +169 | −36 | −51 |
| Cat. No. 2 | not recorded | 4 | +236 | +31 | −38.5 |
| " | 23 | 1 | +122 | −49.6 | +38.5 |
| " | 24 | 8 | +158 | −45 | −29.5 |
| " | 25 | 0.5 | +52 | −29 | +14 |
| " | 18 | 2 | +9 | −20.5 | +60 |
| 6-trifluoromethyl-2(1H), 3(4H)-quinoxalinedione: Cat No. 1 | — | 0.5 | −25 | −21 | no change |
| " | — | 1 | −50 | +95 | +116 |
| " | — | 2 | −55 | +110 | +113 |
| " | — | 4 | +50 | −97 | −100 |
| " | — | 8 | down slightly | +48 | +43 |
| " | — | 16 | −38 | +201 | no change |
| Cat No. 2 | — | 1 | +7 | −26 | no change |
| " | — | 2 | +20 | −26 | no change |
| " | — | 4 | −39 | +980 | — (2.3% of total time in REM, no REM in control) |
| " | — | 8 | +10 | +52 | — |
| " | — | 16 | +9 | −40 | −100 |

TABLE II-continued

| Compound | Sleep latency in min. | Dose in mg./kg. | Percent Change Awake | SWS | REM |
|---|---|---|---|---|---|
| Cat No. 3 | — | 0.5 | −25 | +50 | no change |
| " | — | 1 | −55 | +69 | +59 |
| " | — | 2 | down slightly | +42 | no change |
| " | — | 4 | " | +22 | −10 |
| " | — | 8 | −50 | +62 | +14 |
| " | — | 16 | −43 | +96 | −33 |
| Cat No. 4 | — | 1 | −45 | +63 | −10 |
| " | — | 2 | −70 | +100 | +14 |
| " | — | 4 | no change | +10 | −8 |
| " | — | 8 | −39 | no change | no change |
| " | — | 16 | −51 | no change | −44 |
| Cat No. 5 | — | 0.5 | +200 | −33 | −43 |
| " | — | 1 | +30 | +11 | +34 |
| " | — | 2 | +130 | −21 | −12 |
| " | — | 4 | +52 | +12 | −11 |
| " | — | .8 | −59 | +41 | no change |
| " | — | 16 | no change | +29 | −11 |
| Cat No. 6 | — | 0.5 | +51 | −12 | −37 |
| " | — | 1 | −20 | +14 | +34 |
| " | — | 2 | −11 | +60 | −67 |
| " | — | 4 | −67 | +132 | +200 |
| " | — | 8 | −31 | +112 | −67 |
| " | — | 16 | +67 | −16 | −100 |
| Cat No. 7 | — | 1 | +100 | −23 | −100 |
| " | — | 2 | −60 | +85 | no change |
| " | — | 4 | −20 | no change | no change |
| " | — | 8 | −55 | +430 | no change |
| " | — | 16 | +28 | −20 | −100 |
| Cat No. 8 | — | 1 | +20 | +22 | −48 |
| " | — | 2 | up slightly | +20 | −21 |
| " | — | 4 | +33 | −35 | −20 |
| " | — | 8 | +30 | +9 | −54 |
| " | — | 16 | +70 | −66 | −47 |

EXAMPLE 68

6-Trifluoromethyl-2(1H), 3(4H)-quinoxalinedione was evaluated in the same procedures reported in Examples 63–67, except that the time period was longer (7 ½ hours instead of 2 hours, 10 minutes); and only one dose was employed (2 mg./kg.) but it was administered to each of three cats. Results for the three cats were averaged, and were recorded (1) for the first 2 ½ hours (2) for the first 5 hours and (3) for the entire 7 ½ hour period. The results were as set forth in the following table.

TABLE III

| Time Period | Percent Change Awake | SWS | REM |
|---|---|---|---|
| First 2½ hrs. | −13 | +49 | +91 |
| First 5 hrs. | −18 | +35 | +39 |
| Entire 7½ hrs. | −11 | +18 | +25 |

The compounds to be employed as starting materials are prepared in conventional procedures, and some are commercially available. Those starting materials which are o-phenylenediamines are prepared in accordance with the following reaction scheme:

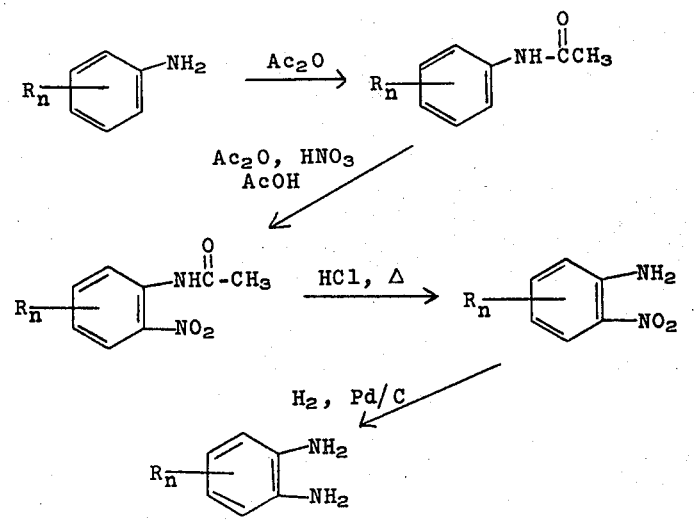

A representative preparation follows.

p-Ethylaniline (50 grams) was added portionwise to 100 grams of acetic anhydride. Considerable heat was evolved. After standing one hour, the solution was poured into 500 ml. of water. The resulting mixture was warmed on a steam bath with occasional swirling, to decompose excess anhydride, then chilled overnight. The p-ethylacetanilide product was separated by filtration and recrystallized from ethanol-water, m.p. 86°–88.5°C.

A mixture of fuming nitric acid (1.4 ml.) and acetic acid (2 ml.) was added portionwise to a stirred 0°C. solution of p-ethylacetanilide (4.0 grams) in acetic anhydride (4.2 ml.) and acetic acid (4.4 ml.). The temperature was allowed to rise slowly to 25°C. Subsequently the reaction mixture was poured into 100 ml. of water. An oil settled but did not crystallize. The mixture was extracted with ether and evaporated, leaving the 2'-nitro-4'-ethylacetanilide as a dark oil.

This oil was used directly in the next reaction. It was refluxed for one hour in a mixture of 50 ml. of 6N hydrochloric acid and 15 ml. of ethanol. The reaction mixture was then cooled, neutralized, and extracted with ethyl acetate. Decolorization, drying over sodium sulfate, and evaporation yielded 2-nitro-4-ethylaniline as a dark oil which solidified. Its identity was confirmed by IR.

The crude 2-nitro-4-ethylaniline was hydrogenated in 100 ml. of ethanol over 500 mg. of 5 percent palladium on charcoal, until gas uptake ceased. The reaction mixture was filtered and evaporated, yielding 4-ethyl-o-phenylenediamine as a dark oil which solidified overnight. The identity of the product was confirmed by IR.

In similar procedures, there was prepared 4-trifluoromethyl-o-phenylenediamine, m.p. 55°–57°C.

Those of the starting materials which are of the formula

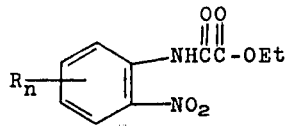

are prepared by the following reaction scheme;

In a representative preparation, ethyl N-(4-difluoromethyl-2-nitrophenyl)oxamide was prepared as described below.

p-Nitrobenzal fluoride (5 grams) (prepared by reaction of p-nitrobenzaldehyde with $SF_4/HF$) was hydrogenated over 200 mg. platinum oxide in 50 ml. of ethanol. The catalyst was removed by filtration and the ethanol, by evaporation. The residue was dissolved in 50 ml. of cold ether; to this solution was added a solution of ethyl oxalyl chloride (7 ml.) in 25 ml. of ether. The reaction mixture was stirred for 15 minutes, filtered, and evaporated to dryness. The residue, the desired ethyl N-(p-difluoromethylphenyl)oxamide product, was recrystallized from a mixture of ethanol and water, m.p. 110°–114°C. Ethyl N-(p-difluoromethylphenyl)oxamide (1 gram) was dissolved in 4 ml. of each of acetic acid and acetic anhydride and the mixture cooled to about 0°–5°C. Fuming nitric acid (1 ml.) mixed with acetic acid (2 ml.) was added portionwise to the cooled solution. An additional 1 ml. of fuming nitric acid was added one hour later. Two hours after the initial addition, the reaction mixture was poured into water, and the ethyl N-(4-difluoromethyl-2-nitrophenyl)oxamide product was collected, washed, and recrystallized from a mixture of ethanol and water, m.p. 113°–115°C.

Those starting materials which are 1-methylquinoxalinones:

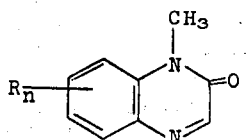

are prepared in accordance with the following procedures

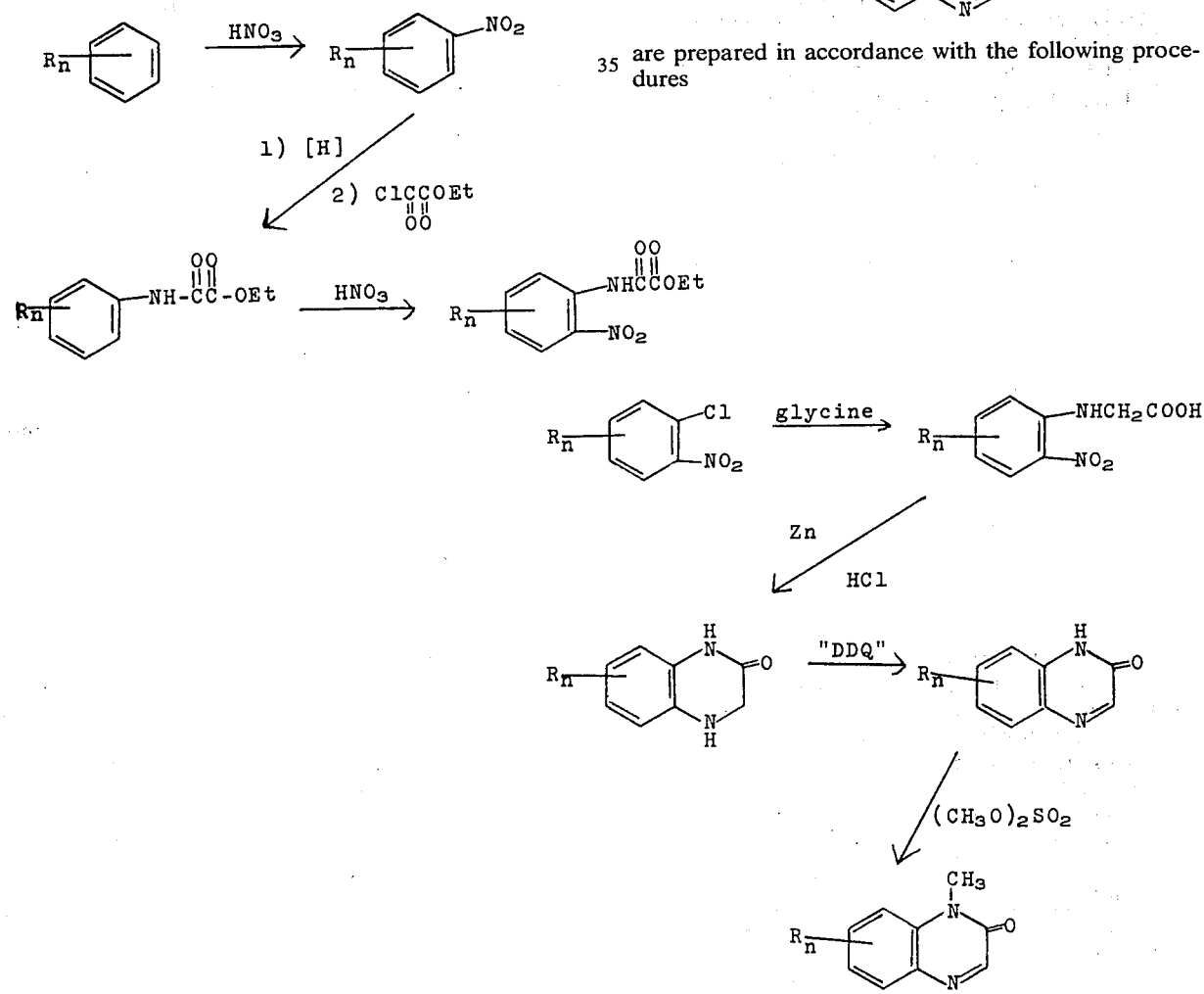

The following preparation of 1-methyl-7-trifluoromethyl-2(1H)-quinoxalinone illlustrates the procedure.

4-Chloro-3-nitrobenzotrifluoride (10 grams), glycine (7 grams), and potassium carbonate (10 grams) were mixed in a mixture of 40 ml. each of water and dimethyl sulfoxide. The mixture was heated to 80°–100°C. and held for 6 hours, then poured into 600 ml. of water, acidified, and chilled to 5°C. The mixture was filtered, yielding N-(2-nitro-4-trifluoromethylphenyl)-glycine. The product was dissolved in 5 percent sodium bicarbonate and reprecipitated by acidification. It was separated and recrystallized from a mixture of ethanol and water, m.p., 167°–170°C.

The N-(2-nitro-4-trifluoromethylphenyl)glycine (5.0 grams) was dissolved in 60 ml. of acetic acid at room temperature. There was then added 10 ml. of concentrated hydrochloric acid and 4.0 grams of zinc dust, the first half of the zinc dust was added in portions, the second half, in one batch. The reaction mixture was stirred about 30 minutes, then filtered and diluted to 750 ml. The 3,4-dihydro-7-trifluoromethyl-2(1H)-quinoxalinone was separated by filtration, m.p. 186°–189°C.

The 3,4-dihydro-7-trifluoromethyl-2(1H)-quinoxalinone (3.4 grams) and 2,3-dichloro-5,6-dicyanobenzoquinone (4.0 grams) were refluxed for 1.5 hours in 200 ml. of ethyl acetate. The reaction mixture was then evaporated to dryness, chromatographed on silica gel (500 grams), and the 7-trifluoromethyl-2(1H)-quinoxalinone recrystallized from a mixture of ethanol and water, m.p., 204°–206°C.

7-Trifluoromethyl-2(1H)-quinoxalinone (about 5 grams) was dissolved in 80 ml. of 1N sodium hydroxide and the mixture stirred with 15 grams of dimethyl sulfate. The 1-methyl-7-trifluoromethyl-2(1H)-quinoxalinone product crystallized and was separated and recrystallized from ethanol, m.p. 153°–155°C.

We claim:

1. A method for causing a hypnotic effect in a warm-blooded animal which comprises administering to a warm-blooded animal suffering from insomnia an effective amount of an active agent selected from the group consisting of a compound of the formula

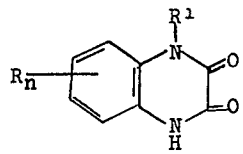

wherein $n$ represents 0, 1, or 2; each R independently represents
1. loweralkyl of $C_1$–$C_4$,
2. loweralkoxy of $C_1$–$C_4$,
3. loweralkylthio of $C_1$–$C_4$,
4. cyclopropyl,
5. bromo,
6. chloro,
7. fluoro,
8. nitro,
9. cyano,
10. fluoroalkyl of $C_1$–$C_2$,
11. amino, or
12. amino mono or disubstituted with loweralkyl of $C_1$–$C_4$, each independently selected;

subject to the limitation that R can represent bromo or chloro only when $n$ represents 2 and one R represents a moiety other than bromo or chloro; and $R^1$ represents
1. H or
2. methyl;

and a pharmaceutically acceptable alkali metal or alkaline earth metal salt.

2. The method of claim 1 wherein the warm-blooded animal is a human being.

3. The method of claim 2 wherein the active agent is 6-trifluoromethyl-2(1H), 3(4H)-quinoxalinedione or a pharmaceutically acceptable alkali metal or alkaline earth metal salt.

4. The method of claim 3 wherein the active agent is 6-trifluoromethyl-2(1H), 3(4H)-quinoxalinedione.

5. The method of claim 3 wherein the active agent is 6-trifluoromethyl-2(1H), 3(4H)-quinoxalinedione monopotassium salt.

6. The method of claim 2 wherein the active agent is 6-methyl-2(1H), 3(4H)-quinoxalinedione or a pharmaceutically acceptable alkali metal or alkaline earth metal salt.

7. The method of claim 2 wherein the active agent is 6-ethyl-2(1H), 3(4H)-quinoxalinedione or a pharmaceutically acceptable alkali metal or alkaline earth metal salt.

8. The method of claim 2 wherein the active agent is 5-methyl-2(1H), 3(4H)-quinoxalinedione or a pharmaceutically acceptable alkali metal or alkaline earth metal salt.

9. The method of claim 2 wherein the active agent is 2(1H), 3(4H)-quinoxalinedione or a pharmaceutically acceptable alkali metal or alkaline earth metal salt.

10. A method for causing a hypnotic effect in a warm-blooded animal which comprises administering to a warm-blooded animal in which it is desired to induce sleep an effective amount of an active agent selected from the group consisting of a compound of the formula

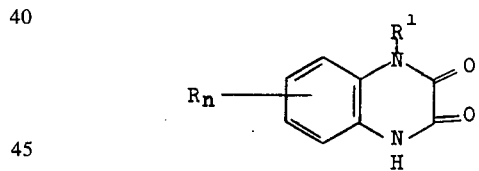

wherein $n$ represents 0, 1, or 2; each R independently represents
1. loweralkyl of $C_1$–$C_4$,
2. loweralkoxy of $C_1$–$C_4$,
3. loweralkylthio of $C_1$–$C_4$,
4. cyclopropyl,
5. bromo,
6. chloro,
7. fluoro,
8. nitro,
9. cyano,
10. fluoroalkyl of $C_1$–$C_2$,
11. amino, or
12. amino mono or disubstituted with loweralkyl of $C_1$–$C_4$, each independently selected;

subject to the limitation that R can represent bromo or chloro only when $n$ represents 2 and one R represents a moiety other than bromo or chloro; and $R^1$ represents
1. H or
2. methyl;

and a pharmaceutically acceptable alkali metal or alkaline earth metal salt.

11. The method of claim 10 wherein the warm-blooded animal is a human being.

12. The method of claim 11 wherein the active agent is 6-trifluoromethyl-2(1H), 3(4H)-quinoxalinedione or a pharmaceutically acceptable alkali metal or alkaline earth metal salt.

13. The method of claim 12 wherein the active agent is 6-trifluoromethyl-2(1H), 3(4H)-quinoxalinedione.

14. The method of claim 12 wherein the active agent is 6-trifluoromethyl-2(1H), 3(4H)-quinoxalinedione monopotassium salt.

15. The method of claim 11 wherein the active agent is 6-methyl-2(1H), 3(4H)-quinoxalinedione or a pharmaceutically acceptable alkali metal or alkaline earth metal salt.

16. The method of claim 11 wherein the active agent is 6-ethyl-2(1H), 3(4H)-quinoxalinedione or a pharmaceutically acceptable alkali metal or alkaline earth metal salt.

17. The method of claim 11 wherein the active agent is 5-methyl-2(1H), 3(4H)-quinoxalinedione or a pharmaceutically acceptable alkali metal or alkaline earth metal salt.

18. The method of claim 11 wherein the active agent is 2(1H), 3(4H)-quinoxalinedione or a pharmaceutically acceptable alkali metal or alkaline earth metal salt.

19. A pharmaceutical formulation in dosage unit form adapted for administration to obtain a hypnotic effect, comprising per dosage unit, a hypnotically-effective non-toxic amount within the range from about 10 to about 1000 milligrams of at least one active agent selected from the group consisting of a compound of the formula

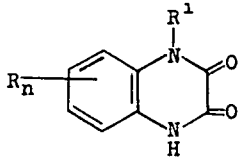

wherein $n$ represents 0, 1, or 2; each R independently represents
1. loweralkyl of $C_1$–$C_4$,
2. loweralkoxy of $C_1$–$C_4$,
3. loweralkylthio of $C_1$–$C_4$,
4. cyclopropyl,
5. bromo,
6. chloro,
7. fluoro,
8. nitro,
9. cyano,
10. fluoroalkyl of $C_1$–$C_2$,
11. amino, or
12. amino mono or disubstituted with loweralkyl of $C_1$–$C_4$, each independently selected;

subject to the limitation that R can represent bromo or chloro only when $n$ represents 2 and one R represents a moiety other than bromo or chloro; and $R^1$ represents
1. H or
2. methyl;

and a pharmaceutically acceptable alkali metal or alkaline earth metal salt and a pharmaceutically acceptable carrier therefor.

20. The formulation of claim 19 wherein the active agent is 6-trifluoromethyl-2(1H), 3(4H)-quinoxalinedione or a pharmaceutically acceptable alkali metal or alkaline earth metal salt.

21. The formulation of claim 20 wherein the active agent is 6-trifluoromethyl-2(1H), 3(4H)-quinoxalinedione.

22. The formulation of claim 20 wherein the active agent is 6-trifluoromethyl-2(1H), 3(4H)-quinoxalinedione monopotassium salt.

* * * * *